United States Patent [19]

Manabe et al.

[11] 4,001,313

[45] Jan. 4, 1977

[54] MANUFACTURE OF AROMATIC AMINO COMPOUNDS

[75] Inventors: Osamu Manabe; Kenichi Nara, both of Osaka, Japan

[73] Assignee: Osaka City, Osaka, Japan

[22] Filed: Sept. 26, 1974

[21] Appl. No.: 509,631

Related U.S. Application Data

[63] Continuation of Ser. No. 210,215, Dec. 20, 1971, abandoned.

[30] Foreign Application Priority Data

Dec. 29, 1970 Japan .............................. 45-127299

[52] U.S. Cl. ..................... 260/508; 260/509; 260/510; 260/518 R; 260/578; 260/581; 260/558 A

[51] Int. Cl.$^2$ ................ C07C 143/56; C07C 85/02; C07C 101/44

[58] Field of Search .............. 260/508, 510, 518 R, 260/578, 581, 585 R, 558 A, 509; 210/215

[56] References Cited

UNITED STATES PATENTS

| | | | |
|---|---|---|---|
| 2,000,411 | 5/1935 | Morrell et al. | 260/578 |
| 2,106,180 | 1/1938 | Kreimer | 260/635 Y |

OTHER PUBLICATIONS

Houben–Weyl, "Methoden der Organischen Chemie," 11(1), pp. 246–247 (1957).
Bergstrom, J. Org. Chem., 3, 233 (1938).
Fieser et al., "Reagents for Organic Synthesis", pp. 1034–1040 (1967).

*Primary Examiner*—James O. Thomas, Jr.
*Assistant Examiner*—Nicky Chan
*Attorney, Agent, or Firm*—Larson, Taylor and Hinds

[57] ABSTRACT

A process for producing an aromatic amine comprises heating an aromatic sulfonate and a metal amide in liquid ammonia in a closed reactor at a temperature of at least 40° C to produce a metal arylamide and reacting the resultant metal arylamide with water or lower aliphatic alcohol to produce an aromatic amine.

8 Claims, No Drawings

MANUFACTURE OF AROMATIC AMINO COMPOUNDS

This is a cont. of appl. Ser. No. 210,215 filed Dec. 20, 1971 (now abandoned).

This invention relates to manufacture of aromatic amino compounds, more particularly to an improved method for producing aromatic amino compounds from aromatic sulfonates and metal amides.

The reaction between aromatic sulfonates and metal amides to produce aromatic amino compounds is known in the art. In the known method, the reaction is usually conducted at an elevated temperature of about 200° C using molten naphthalene as a solvent. According to this method it is difficult to obtain the aromatic amino compounds in a yield of more than 30% due to undesired side reactions, such as decomposition, polymerization, etc., hence impractical from industrial viewpoints.

Main object of the invention is to provide a method for producing aromatic amino compounds from aromatic sulfonates and metal amides in a high order of yield free from undesired side reactions.

This and other objects and advantages of the invention will be apparent from the following description.

The process for producing an aromatic amino compound according to the present invention comprises heating an aromatic sulfonate and a metal amide in liquid ammonia in a closed reactor at a temperature of at least 40° C to produce a metal arylamide, reacting the resultant metal arylamide with water or lower aliphatic alcohol to produce an aromatic amine and separating the aromatic amine thus produced from the reaction mixture.

According to the researches of the present inventors it has been found that when the reaction between aromatic sulfonates and metal amides to produce aromatic amino compounds is conducted in liquid ammonia the aromatic amino compounds can be obtained in a high order to yield without being accompained by undesired side reactions. In fact, a high yield of more than 75% can be ensured in accordance with the present invention.

The reaction involved in the present invention can be represented in the following equations in which sodium benzene sulfonate and sodium amide are used as a starting material.

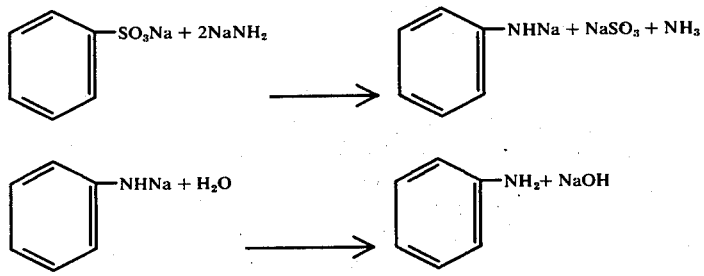

The starting aromatic sulfonates used in the invention include, for example, sodium salt, potassium salt and like alkali metal salts, calcium salt, barium salt and like alkaline earth metal salts and ammonium salt. The aromatic sulfonic acids include those having the following formula:

$$A-(SO_3H)_n$$

wherein $n$ is an integer of 1 to 4 and A is a benzene, naphthalene, anthracene or pyrene ring having or not having 1 to 5 substitutes, said substitute being an alkyl of 1 to 4 carbon atoms, aminoalkyl of 1 to 4 carbon atoms, hydroxyalkyl of 1 to 4 carbon atoms, carboxyalkyl of 2 to 5 carbon atoms, phenylalkyl of 7 to 10 carbon atoms, phenyl, alkylphenyl of 7 to 13 carbon atoms, carboxyl, carbonamide, amino, hydroxyl or styryl. Examples of the aromatic sulfonates are benzene sulfonate, toluene sulfonate, tertiarybutylbenzene sulfonate, octylbenzene sulfonate, xylene sulfonate (e.g. 4-o-, 4-m, 5-m-or 2-p-xylene sulfonate), trimethylbenzene sulfonate, phenylbenzene sulfonate, (2-hydroxyethyl)benzene sulfonate, carboxymethylbenzene sulfonate, benzylbenzene sulfonate, (2-aminoethyl)benzene sulfonate, carboxybenzene sulfonate, styrylbenzene sulfonate, naphthalene sulfonate, naphthalene disulfonate, naphthalene trisulfonate, aminonaphthalene sulfonate, naphthol sulfonate, anthracene sulfonate, pyrene sulfonate and the like. In accordance with the present invention, from the monosulfonates the corresponding monoamines can be obtained, and from the polysulfonates the corresponding polyamines or partially aminated products can be obtained.

When xylene sulfonate, naphthol sulfonate, tertiarybutylbenzene sulfonate, naphthalene disulfonate, carboxybenzene sulfonate or the like was used as a starting aromatic sulfonate in the prior methods, for example, it was unavoidable to produce a large amount of isomers which were useless and difficult to separate from the product, or many complicated steps were required. However, according to the present invention the desired aromatic amines can be easily obtained even from such aromatic sulfonates in a high order of yield in a single step of the reaction. Therefore, the present process is particularly effective on the production of aromatic amines from such sulfonates.

The metal amides used in the invention include lithium amide, sodium amide, potassium amide and like alkali metal amides and calcium amide, barium amide and like alkaline earth metal amides. Of these sodium amide and potassium amide are preferable. The metal amides are employed in theoretical amount or in excess amount. Preferably it is used in an amount of 2 to 2.2 moles per sulfonyl group of the aromatic sulfonate.

In accordance with the present invention it is essential to carry out the reaction using liquid ammonia as a solvent, whereby the reaction to produce aromatic amino compounds is markedly accelerated with effective prevention of undesired side reaction, thus making it possible to obtain aromatic amino compounds in a high order of yield. The amount of liquid ammonia used may vary over a wide range in accordance with the kinds of aromatic sulfonate used as a starting material, but it is usually employed in an amount of 10 to 80 times the mole of the starting aromatic sulfonate. Preferable amount is in the range of 20 to 40 times the mole of the aromatic sulfonate.

According to the present invention the reactants and liquid ammonia are placed in a closed pressure-reactor such as autoclave and the like, and the mixture is heated in the reactor at a temperature of not less than 40° C. When temperature is lower than 40° C the reaction can not proceed effectively. The reaction velocity increases with the reaction temperature applied but a temperature of above 300° C highly increases the pressure in the reactor and is liable to promote undesired side reactions. Therefore, a temperature ranging from 40° to 300° C is usually applied. Preferable reaction temperature is 100° to 200° C. The pressure in the autoclave is a saturated pressure of the liquid ammonia at a temperature lower than the critical temperature of ammonia and varies in accordance with the amount of ammonia used at a temperature higher than the critical temperature thereof. It is preferable to carry out the reaction in an atmosphere substantially free of water. Although the reaction period may vary over a wide range in accordance with the kinds of the starting materials, temperature applied and other factors, the reaction usually completes within 2 to 20 hours.

After removal of ammonia from the resultant reaction mixture, the reaction product thus obtained is then solvolyzed with water or lower aliphatic alcohol to produce the desired amine. Examples of the lower alcohol are methanol, ethanol and propanol. The solvolysis is usually conducted at room temperature, though it may be carried out under cooling. The amount of water or alcohol to be used may vary over a wide range and is not critical, since the product, i.e. metal arylamide is easily hydrolysed with water in air and the use of a large excess amount thereof gives no adverse affect on the product. But it is preferable to use water or alcohol in stoichiometric amounts or in excess amount.

The resultant amine can be separated from the reaction mixture by conventional methods, for example, by extraction with organic solvents such as ether, benzene, etc. and/or recrystallization.

For a better understanding of the invention examples are given below. As can be seen from the examples, a preferred temperature range is 70° to 200° C and a preferred molar ratio of metal amide is in an amount of about 2.1 to 3.6 moles per sulfonyl group of the aromatic sulfonate.

EXAMPLE 1

In a 200-ml autoclave were placed 33 grams (0.18 mole) of anhydrous sodium benzene sulfonate and 15 grams (0.38 mole) of sodium amide and the air in the autoclave was removed by a vacuum pump. The autoclave was then cooled at −50° to −60° C and 100 ml of liquid ammonia was charged to the autoclave. After the termination of cooling the reaction mixture in the autoclave was heated at 100° C for 9 hours. The pressure in the autoclave was 62 atm. during the reaction. Thereafter the ammonia was distilled off and liquified for recovery. To the resultant reaction mixture 20 ml of water was added for hydrolysis. The product was extracted with ether and the ether was distilled off to produce crude aniline. The further distillation thereof gave 16 grams of aniline boiling at 184° to 186° C. Yield was 88.3%.

EXAMPLE 2

In a 200-ml autoclave were placed 35 grams (0.163 moles) of anhydrous sodium 4-o-xylene sulfonate, 14 grams (0.35 mole) of sodium amide and 120 ml of liquid ammonia in the same manner as in Example 1. The resultant mixture was heated at 120° to 125° C for 15 hours. The reaction pressure in the autoclave was 90 to 100 atm. during the reaction. After the ammonia was removed, 15 ml of methanol was added to the reaction mixture for solvolysis. Thereafter 500 ml of water was added to the product and the mixture was treated in the same manner as in Example 1, whereby 17.4 grams of 3,4-xylidine boiling at 112° C/22 mm Hg was obtained. Yield was 88.1%.

EXAMPLE 3

In a 200-ml autoclave were placed 28.3 grams (0.115 mole) of anydrous potassium 1-naphthalene sulfonate, 9.7 grams (0.241 mole) of sodium amide and 105 ml of liquid ammonia in the same manner as in Example 1. The resultant mixture was heated at 110° C for 10 hours. The reaction pressure in the autoclave was 75 atm. during the reaction. After the ammonia was removed, 10 ml of water was added to the reaction mixture for hydrolysis. The product was extracted with ether and the ether was distilled off to produce crude 1-naphthyl amine. Recrystallization from ethanol gave 14.3 grams of 1-naphthyl amine having a melting point of 48° to 49° C. Yield ws 87.0%.

EXAMPLE 4

In a 200-ml autoclave were placed 24 grams (0.120 mole) of anhydrous sodium p-toluene sulfonate, 11 grams (0.275 mole) of sodium amide and 75 ml of liquid ammonia in the same manner as in Example 1. The resultant mixture was heated at 110° to +° C for 10 hours. The reaction pressure in the autoclave was 75 to 80 atm. during the reaction. After the ammonia was removed, 10 ml of water was added to the reaction mixture for hydrolysis. Thereafter the product was treated in the same manner as in Example 1, whereby 11.3 grams of p-toluidine having a boiling point of 200° to 201° C and melting point of 44° to 45° C was obtained. Yield was 87.7%.

EXAMPLE 5

In a 200-ml autoclave were placed 36.5 grams (0.107 mole) of anhydrous sodium 1,5-naphthalene disulfonate, 9 grams (0.225 mole) of sodium amide and 100 ml of liquid ammonia in the same manner as in Example 1. The resultant mixture was heated at 115° C for 12 hours. The reaction pressure in the autoclave was 85 atm. during the reaction. 100 ml of water was added to the reaction mixture and the product was extracted with ether. To the water layer was added dilute hydrochloric acid to precipitate crude 1-naphthylamine-5-sulfonic acid. The precipitated acid was neutralized with sodium hydroxide and recrystallized from water, whereby 23.6 grams of sodium 1-naphthylamine-5-sulfonate was obtained. Yield was 87.5%.

Elementary analysis of the 1-naphthylamine5-sulfonic acid gave the following results:

Found: N, 6.27%. Calcd. for $C_{10}H_9NO_3S$: N, 6.24%.

EXAMPLE 6

In a 200-ml autoclave were placed 26.6 grams (0.08 mole) of anhydrous sodium 1,5-naphthalene disulfonate, 17.6 grams (0.44 mole) of sodium amide and 80 ml of liquid ammonia in the same manner as in Example 1. The resultant mixture was heated at 180° C for 10 hours. The reaction pressure in the autoclave was 160 atm. during the reaction. After the ammonia was removed 30 ml of methanol was added to the reaction mixture for solvolysis. Thereafter the product was treated in the same manner as in Example 2, whereby 10.7 grams of 1,5-diaminonaphthalene was obtained. Yield was 84.5%.

EXAMPLE 7

In a 200-ml autoclave were placed 27.4 grams (0.119 mole) of anhydrous sodium 2-naphthalene sulfonate, 10 grams (0.25 mole) of sodium amide and 80 ml of liquid ammonia in the same manner as in Example 1. The resultant mixture was heated at 120° C for 10 hours. The reaction pressure in the autoclave was 90 atm. during the reaction. After the ammonia was removed, 15 ml of water was added to the reaction mixture for hydrolysis. The product was extracted with ether and the ether was distilled off to produce crude 2-naphthylamine. Recrystallization from methanol gave 14.6 grams of 2-naphthylamine having a melting point of 111° to 112° C. Yield was 85.7%.

EXAMPLE 8

4.2 grams of sodium was dissolved in 130 ml of liquid ammonia placed in a 200-ml autoclave. To the solution was added 500 mg of ferric nitrate and the mixture was stirred at −50° to −60° C for 1.5 hours to produce sodium amide. To the resultant mixture was added 12 grams of the anhydrous sodium p-toluene sulfonate and the mixture was heated at 115° C for 12 hours. The pressure in the autoclave was 85 atm. during the reaction. The product thus obtained was treated in the same manner as in Example 1, whereby 5.5 grams of p-toluidine having a melting point of 44° to 45° C was obtained. Yield was 86.0%.

EXAMPLE 9

In a 200-ml autoclave were placed 34 grams (0.11 mole) of anhydrous calcium 4-tertiarybutylbenzene sulfonate, 9.6 grams (0.24 mole) of sodium amide and 120 ml of liquid ammonia in the same manner as in Example 1. The resultant mixture was heated at 140° C for 8 hours. The reaction pressure in the autoclave was 123 atm. during the reaction. After the ammonia was removed, 10 ml of water was added to the reaction mixture for hydrolysis. Thereafter the product was treated in the same manner as in Example 1, whereby 13.2 grams of 4-tertiarybutyl aniline boiling at 114° to 115° C/10 mm Hg was obtained. Yield was 80.6%.

EXAMPLE 10

In a 200-ml autoclave were placed 11.2 grams (0.05 mole) of anydrous sodium 2,3,5-trimethylbenzene sulfonate, 5.2 grams (0.13 mole) of sodium amide and 60 ml liquid ammonia in the same manner as in Example 1. The resultant mixture was heated at 160° C for 9 hours. The reaction pressure in the autoclave was 140 atm. during the reaction. After the ammonia was removed, 10 ml of water was added to the reaction mixture for hydrolysis. The product was extracted with ether and the ether was distilled off to produce crude 2,3,5-trimethyl aniline. The recrystallization thereof from petroleum ether gave 5.3 grams of 2,3,5-trimethyl aniline having a melting point of 36° C. Yield was 78.8%.

EXAMPLE 11

In a 200-ml autoclave were placed 28.8 grams (0.12 mole) of anhydrous potassium p-carboxybenzene sulfonate, 21 grams (0.38 mole) of potassium amide and 80 ml of liquid ammonia in the same manner as in Example 1. The resultant mixture was heated at 180° C for 8 hours. The reaction pressure in the autoclave was 160 atm. during the reaction. After the ammonia was removed, 10 ml of ethanol was added to the reaction mixture for solvolysis. Thereafter the product was treated in the same manner as in Example 2, whereby 13.7 grams of p-aminobenzoic acid having a melting point of 186° to 187° C was obtained. Yield was 83.3%.

EXAMPLE 12

In a 200-ml autoclave were placed 29.2 grams (0.13 mole) of anhydrous sodium 1-aminonaphthalene-5-sulfonate, 13.2 grams (0.33 mole) of sodium amide and 110 ml of liquid ammonia in the same manner as in Example 1. The resultant mixture was heated at 200° C for 5 hours. The reaction pressure in the autoclave was 180 atm. during the reaction. After the ammonia was removed, 50 ml of methanol was added to the reaction mixture for solvolysis. The product was extracted with chloroform and the chloroform was distilled off to produce crude 1,5-diaminonaphthaline. The recrystallization thereof from ether gave 18.4 grams of 1,5-diaminonaphthalene having a melting point of 187° to 189.5° C. Yield was 89.1%.

EXAMPLE 13

In a 200-ml autoclave were placed 18.6 grams (0.06 mole) of anhydrous sodium p-styrylbenzene sulfonate, 5.2 grams (0.13 mole) of sodium amide and 50 ml of liquid ammonia in the same manner as in Example 1. The resultant mixture was heated at 120° C for 6 hours. The reaction pressure in the autoclave was 90 atm. during the reaction. After the ammonia was removed, 10 ml of water was added to the reaction mixture for hydrolysis. The product was extracted with ether and the ether was distilled off to produce crude 4-aminostilbene. The recrystallization thereof from ethanol gave 11.9 grams of 4-aminostilbene having a melting point of 151° to 152° C. Yield was 88.5%.

EXAMPLE 14

In a 200-ml autoclave were placed 12 grams (0.05 mole) of anhydrous potassium p-(2-aminoethyl)benzene sulfonate, 6.1 grams (0.11 mole) of potassium amide and 55 ml of liquid ammonia in the same manner as in Example 1. The resultant mixture was heated at 135° C for 5 hours. The reaction pressure in the autoclave was 115 atm. during the reaction. After the ammonia was removed, 10 ml of water was added to the reaction mixture for hydrolysis. The product was extracted with ether and the ether was distilled off to produce crude 4-(2-aminoethyl)aniline. The recrystallization thereof from ether gave 5.6 grams of 4-(2-aminoethyl)aniline having a melting point of 62° to 63° C and boiling point of 140° to 142° C/12 mm Hg. Yield was 82.5%.

EXAMPLE 15

In a 200-ml autoclave were placed 27.6 grams (0.96 mole) of anhydrous barium p-phenylbenzene sulfonate, 6 grams (0.15 mole) of sodium amide and 80 ml of liquid ammonia in the same manner as in Example 1. The resultant mixture was heated at 120° C for 5 hours. The reaction pressure in the autoclave was 90 atm. during the reaction. After the ammonia was removed, 15 ml of methanol was added to the reaction mixture for solvolysis. Thereafter the product was treated in the same manner as in Example 2, whereby 8.5 grams of p-phenylaniline having a melting point of 53° C. Yield was 83.5%.

EXAMPLE 16

In a 200-ml autoclave were placed 13.5 grams (0.05 mole) of anhydrous sodium benzylbenzene sulfonate, 5.2 grams (0.13 mole) of sodium amide and 65 ml of liquid ammonia in the same manner as in Example 1. The resultant mixture was heated at 120° C for 10 hours. The reaction pressure in the autoclave was 90 atm. during the reaction. After the ammonia was removed, 10 ml of water was added to the reaction mixture for hydrolysis. Thereafter the product was treated in the same manner as in Example 1, whereby 7.9 grams of p-benzylaniline having a melting point of 34° to 35° C. Yield was 85.8%.

EXAMPLE 17

In a 200-ml autoclave were placed 28.9 grams (0.11 mole) of anhydrous sodium 2-naphthol-8-sulfonate, 14.4 grams (0.36 mole) of sodium amide and 100 ml of liquid ammonia in the same manner as in Example 1. The resultant mixture was heated at 170° C for 8 hours. The reaction pressure in the autoclave was 150 atm. during the reaction. After the ammonia was removed, 30 ml of water was added to the reaction mixture for hydrolysis. Thereafter the product was treated in the same manner as in Example 1, whereby 14.0 grams of 1-amino-7-naphthol having a melting point of 205° to 207° C. Yield was 80.1%.

EXAMPLE 18

In a 200-ml autoclave were placed 30.8 grams (0.11 mole) of anhydrous sodium 1-anthracene sulfonate, 9.2 grams (0.23 mole) of sodium amide and 100 ml of liquid ammonia in the same manner as in Example 1. The resultant mixture was heated at 100° C for 8 hours. The reaction pressure in the autoclave was 62 atm. during the reaction. After the ammonia was removed, 20 ml of water was added to the reaction mixture for hydrolysis. Thereafter the product was treated in the same manner as in Example 1, whereby 17.9 grams of 1-aminoanthracene having a melting point of 127° C was obtained. Yield was 84.2%.

EXAMPLE 19

In a 200-ml autoclave were placed 21.3 grams (0.07 mole) of anhydrous sodium 2-pyrene sulfonate, 8.8 grams (0.16 mole) of potassium amide and 70 ml of liquid ammonia in the same manner as in Example 1. The resultant mixture was heated at 105° C for 6 hours. The reaction pressure in the autoclave was 65 atm. during the reaction. After the ammonia was removed, 20 ml of ethanol was added to the reaction mixture for solvolysis. Thereafter the product was treated in the same manner as in Example 2, whereby 16.2 grams of 2-aminopyrene having a melting point of 128° to 130° C was obtained. Yield was 82.8%.

EXAMPLE 20

In a 200-ml autoclave were placed 29.1 grams (0.15 mole) of anhydrous sodium m-toluene sulfonate, 12.4 grams (0.31 mole) of sodium amide and 60 ml of liquid ammonia in the same manner as in Example 1. The resultant mixture was heated at 150° C for 2.5 hours. The reaction pressure in the autoclave was 132 atm. during the reaction. After the ammonia was removed 20 ml of water was added to the reaction mixture for hydrolysis. Thereafter the product was treated in the same manner as in Example 1, whereby 14.2 grams of m-toluidine having a melting point of 31.0° to 31.5° C and a boiling point of 203° C was obtained. Yield was 88.5%.

EXAMPLE 21

In a 200-ml autoclave were placed 16.7 grams (0.08 mole) of anhydrous sodium 2p-xylene sulfonate, 6.8 grams (0.17 mole) of sodium amide and 70 ml of liquid ammonia in the same manner as in Example 1. The resultant mixture was heated at 150° C for 3 hours. The reaction pressure in the autoclave was 130 atm. during the reaction. After the ammonia was removed 10 ml of water was added to the reaction mixture for hydrolysis. Thereafter the product was treated in the same manner as in Example 1, whereby 8.3 grams of 2,5-xylidine having a boiling point of 103° C/12 mm Hg was obtained. Yield was 85.4%.

EXAMPLE 22

In a 200-ml autoclave were placed 24.7 grams (0.08 mole) of anhydrous sodium p-n-octylbenzene sulfonate, 11 grams (0.20 mole) of potassium amide and 70 ml of liquid ammonia in the same manner as in Example 1. The resultant mixture was heated at 130° C for 5 hours. The reaction pressure in the autoclave was 110 atm. during the reaction. After the ammonia was removed 20 ml of water was added to the reaction mixture for hydrolysis. Thereafter the product was treated in the same manner as in Example 1, whereby 13.7 grams of p-n-octylaniline having a boiling point of 310° to 311° C was obtained. Yield was 83.5%.

EXAMPLE 23

In a 200-ml autoclave were placed 24.7 grams (0.11 mole) of anhydrous sodium p-(2-hydroxyethyl)benzene sulfonate, 13.6 grams (0.34 mole) of sodium amide and 80 ml of liquid ammonia in the same manner as in Example 1. The resultant mixture was heated at 130° C for 6 hours. The reaction pressure in the autoclave was 107 atm. during the reaction. After the ammonia was removed, 20 ml of water was added to the reaction mixture for hydrolysis. Thereafter the product was treated in the same manner as in Example 1, whereby 13.2 grams of p-(2-hydroxyethyl)aniline having a melting point of 108° C was obtained. Yield was 87.6%.

EXAMPLE 24

In a 200-ml autoclave were placed 16.7 grams (0.07 mole) of anhydrous sodium p-(carboxymethyl)benzene sulfonate, 10 grams (0.25 mole) of sodium amide and 60 ml of liquid ammonia in the same manner as in Example 1. The resultant mixture was heated at 110° C for 8 hours. The reaction pressure in the autoclave was 75 atm. during the reaction. After the ammonia was removed, 10 ml of water was added to the reaction mixture for hydrolysis. Thereafter the product was treated in the same manner as in Example 5, whereby 9.7 grams of p-(aminophenyl)acetic acid having a melting point of 200° to 202° C was obtained. Yield was 91.2%.

EXAMPLE 25

In a 200-ml autoclave were placed 26.1 grams (0.06 mole) of anhydrous trisodium 1,36-naphthalene trisulfonate, 5.2 grams (0.13 mole) of sodium amide and 100 ml of liquid ammonia in the same manner as in Example 1. The resultant mixture was heated at 70° C for 5 hours. The reaction pressure in the autoclave was 33 atm. during the reaction. After the ammonia was removed, 10 ml of water was added to the reaction mixture for hydrolysis. Thereafter the product was treated in the same manner as in Example 5, whereby 16.5 grams of 1-aminonaphthalene-3,5-disulfonic acid was obtained. Yield was 90.7%.

Elementary analysis of the product gave the following results: Found N, 4.05%; S, 21.85%. Calcd. for $C_{10}H_9NO_6S_2$: N, 4.62%; S, 21.14%.

EXAMPLE 26

In a 200-ml autoclave were placed 17.9 grams (0.08 mole) of anhydrous sodium m-carbamoylbenzene sulfonate, 9.6 grams (0.24 mole) of sodium amide and 60 ml of liquid ammonia in the same manner as in Example 1. The resultant mixture was heated at 120° C for 7 hours. The reaction pressure in the autoclave was 90 atm. during the reaction. After the ammonia was removed, 10 ml of water was added to the reaction mixture for hydrolysis. Thereafter the product was treated in the same maner as in Example 1, whereby 8.2 grams of m-aminobenzamide having a melting point of 78° to 79° C was obtained. Yield was 75.5%.

EXAMPLE 27

In a 200-ml autoclave were placed 19.6 grams (0.08 mole) of anhydrous sodium 1-aminonaphthalene-8-sulfonate, 10 grams (0.18 mole) of potassium amide and 70 ml of liquid ammonia in the same manner as in Example 1. The resultant mixture was heated at 180° C for 10 hours. The reaction pressure in the autoclave was 160 atm. during the reaction. After the ammonia was removed, 20 ml of water was added to the reaction mixture for hydrolysis. Thereafter the product was treated in the same manner as in Example 1, whereby 9.7 grams of 1,8-diaminonaphthalene having a melting point of 66.5° C was obtained. Yield was 76.4%.

EXAMPLE 28

In a 200-ml autoclave were placed 17.2 grams (0.07 mole) of anhydrous sodium 2-naphthol-6-sulfonate, 9.8 grams (0.25 mole) of sodium amide and 60 ml of liquid ammonia in the same manner as in Example 1. The resultant mixture was heated at 180° C for 9 hours. The reaction pressure in the autoclave was 160 atm. during the reaction. After the ammonia was removed, 20 ml of water was added to the reaction mixture for hydrolysis. Thereafter the product was treated in the same manner as in Example 5, whereby 8.8 grams of 2-amino-6-naphthol having a melting point of 190° to 195° C (decompose) was obtained. Yield was 78.8%.

EXAMPLE 29

In a 200-ml autoclave were placed 22.9 grams (0.11 mole) of anhydrous sodium 5-m-xylene sulfonate, 9.7 grams (0.24 mole) of sodium amide and 80 ml of liquid ammonia in the same manner as in Example 1. The resultant mixture was heated at 150° C for 5 hours. The reaction pressure in the autoclave was 135 atm. during the reaction. After the ammonia was removed, 20 ml of water was added to the reaction mixture for hydrolysis. Thereafter the product was treated in the same manner as in Example 1, whereby 11.3 grams of sym. -m-xylidine boiling at 221° to 222° C was obtained. Yield was 84.4%

What we claim is:

1. A process for producing an aromatic amine which comprises heating an aromatic sulfonate having a formula of

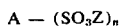

$$A - (SO_3Z)_n$$

wherein Z is selected from the group consisting of alkali metals, alkaline earth metals and ammonium, $n$ is an integer of 1 to 4 and A is a benzene, naphthalene, anthracene or pyrene ring having or not having 1 to 5 substituents, said substituent being an alkyl of 1 to 4 carbon atoms, aminoalkyl of 1 to 4 carbon atoms, hydroxyalkyl of 1 to 4 carbon atoms, carboxyalkyl of 2 to 5 carbon atoms, phenylalkyl of 7 to 10 carbon atoms, phenyl, alkylphenyl of 7 to 13 carbon atoms, carboxyl, carbonamide, amino, hydroxyl or styryl, and a metal amide selected from the group consisting of alkali metal amide and alkaline earth metal amide in liquid ammonia in a closed reactor at a temperature of 70° to 200° C to produce a metal arylamide, removing ammonia from the reaction mixture, reacting the resultant metal arylamide with water or lower alkanol of 1 to 3 carbon atoms to produce an aromatic amine and separating the aromatic amine thus produced from the reaction mixture, said metal amide being used in an amount of about 2.1 to 3.6 moles per sulfonyl group of said aromatic sulfonate.

2. The process according to claim 1 in which the reaction temperature is in the range of 100° C to 200° C.

3. The process according to claim 1, in which said aromatic sulfonate being one member selected from the group consisting of benzene sulfonate, toluene sulfonate, tertiarybutylbenzene sulfonate, octylbenzene sulfonate, xylene sulfonate, trimethylbenzene sulfonate, phenyl benzene sulfonate, (2-hydroxyethyl)benzene sulfonate, carboxymethylbenzene sulfonate, benzylbenzene sulfonate, (2-aminoethyl)benzene sulfonate, carboxybenzene sulfonate, styrylbenzene sulfonate, naphthalene sulfonate, naphthalene disulfonate, naphthalene trisulfonate, aminonaphthalene sulfonate, naphthol sulfonate, anthracene sulfonate and pyrene sulfonate.

4. The process according to claim 3, in which said aromatic sulfonate being one member selected from the group consisting of xylene sulfonate, naphthalene disulfonate, carboxybenzene sulfonate, naphthol sulfonate and tertiarybutylbenzene sulfonate.

5. The process according to claim 1, in which said metal amide is selected from the group consisting of lithium amide, sodium amide, potassium amide, calcium amide and barium amide.

6. The process according to claim 5, in which said metal amide in one member of the group consisting of sodium amide and potassium amide.

7. The process according to claim 1, in which said liquid ammonia is used in an amount of 10 to 80 times the mole of aromatic sulfonate.

8. The process according to claim 7, in which said amount of liquid ammonia is in the range of 20 to 40 times the mole of the aromatic sulfonate.

* * * * *